United States Patent [19]

Bolich, Jr. Raymond E.

[11] Patent Number: 5,002,762

[45] Date of Patent: Mar. 26, 1991

[54] VOLATILE SILICONS IN HOUSEHOLD AND COSMETIC PRODUCTS

[75] Inventor: Bolich, Jr. Raymond E., Maineville, Ohio

[73] Assignee: The Procter & Gamble Company, Cincinnati, Ohio

[21] Appl. No.: 404,719

[22] Filed: Sep. 8, 1989

Related U.S. Application Data

[63] Continuation-in-part of Ser. No. 168,725, Mar. 16, 1988, abandoned.

[51] Int. Cl.$^5$ .............. A61K 7/075; A61K 7/08; A61K 7/11; A61K 7/13
[52] U.S. Cl. .............................. 424/70; 424/64; 424/63; 424/61; 424/59; 424/71; 424/73; 424/65
[58] Field of Search .................. 424/70, 71, 47, 62, 424/64, 69, 59; 252/109

[56] References Cited

U.S. PATENT DOCUMENTS

| | | | |
|---|---|---|---|
| 2,416,504 | 2/1947 | Trautman et al. | 252/49.6 |
| 2,891,980 | 6/1959 | Gilbert et al. | 260/448.2 |
| 4,075,167 | 2/1978 | Takamizawa | 260/46.5 E |
| 4,154,619 | 5/1979 | Pronk | 106/274 |
| 4,207,424 | 6/1980 | Winnick | 585/357 |
| 4,355,062 | 10/1982 | Wang et al. | 428/64 |
| 4,364,837 | 12/1982 | Pader | 424/70 |
| 4,376,087 | 3/1983 | Poliniak et al. | 264/107 |
| 4,391,720 | 7/1983 | Wang et al. | 252/49.6 |
| 4,462,921 | 7/1984 | Peterson et al. | 252/78.3 |
| 4,472,337 | 9/1984 | Huck et al. | 264/107 |
| 4,874,868 | 10/1989 | Bolich | 548/110 |
| 4,902,499 | 2/1990 | Bolich | 424/71 |

FOREIGN PATENT DOCUMENTS

| | | |
|---|---|---|
| 49-108-046 | 10/1974 | Japan . |
| 51-102-019 | 9/1976 | Japan . |
| 56-071-824 | 6/1981 | Japan . |
| 56-139-527 | 10/1981 | Japan . |
| 57-035-526 | 2/1982 | Japan . |

*Primary Examiner*—Thurman K. Page
*Assistant Examiner*—Demetra J. Mills
*Attorney, Agent, or Firm*—David K. Dabbiere; Steven J. Goldstein; Douglas C. Mohl

[57] ABSTRACT

Cosmetic and household products containing volatile silicon compounds which provide good stability and performance are disclosed.

11 Claims, No Drawings

VOLATILE SILICONS IN HOUSEHOLD AND COSMETIC PRODUCTS

This application is a continuation-in-part of U.S. application Ser. No. 168,725, filed Mar. 16, 1988, now abandoned.

BACKGROUND OF THE INVENTION

Volatile silicon compounds have found wide acceptance in a number of different types of products ranging from cosmetics to antifreeze formulations. Such silicon compounds are good solvents for a variety of materials and serve to give excellent feel on skin and hair.

The most common types of volatile silicon compounds are linear and cyclic siloxanes having from one to about seven siloxane groups. While these are the most common, there are other types which have been disclosed. Included among such other silicon compounds are those in U.S. Pat. No. 4,207,424, Winnick, issued June 10, 1980

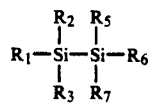

and

Additional disclosures of volatile silicon compounds are in U.S. Pat. No. 4,355,062, Wang et al., issued Oct. 19, 1982. Certain alkyl linear siloxanes such as

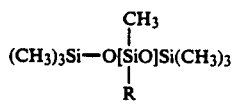

are disclosed in U.S. Pat. No. 4,376,087, Poliniak et al., issued Mar. 8, 1983. Cyclic silicones different from those mentioned above are disclosed in U.S. Pat. No. 4,364,837, Pader, issued Dec. 21, 1982. Still other volatile silicon compounds are disclosed in Japanese unexamined applications JP 9108-046, Oct. 14, 1974; JP 1102-019, Sept. 7, 1976; JP 607-824, June 15, 1981; JP 6139-527, Oct. 31, 1981; and JP 7035-526, Feb. 26, 1982.

Although the references discussed above disclose a variety of volatile silicon compounds in a variety of compositions, there is still the need for cosmetic and household products which incorporate volatile silicon compounds.

It is therefore an object of the present invention to provide cosmetic and household products containing silicon materials which provide improved solvency and compatibility with other composition components.

This and other objectives will become readily available from the detailed disclosure below.

All percentages and ratios herein are by weight unless otherwise specified. Additionally, all measurements are made at 25° C. unless otherwise specified.

SUMMARY OF THE INVENTION

The present invention relates to cosmetic and household products containing volatile silicon compounds of the following structures:

(a) Linear siloxanes

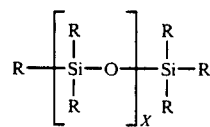

wherein (1) $X = 1$ to 4, (2) total carbons $\leq 14$, (3) R can be independently $C_1$-$C_{10}$ alkyl or trialkyl siloxy, and (4) at least one R per molecule must be selected from aryl, alkylaryl, aryl alkyl, $C_1$-$C_7$ hydroxyalkyl, or —$R_1$-$R_2$ wherein $R_1 = C_1$-$C_9$ alkylene (preferably $C_1$-$C_4$ alkylene) and $R_2$ is selected from

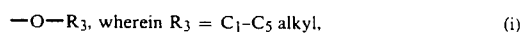  (i)

—O—$R_3$, wherein $R_3$ = $C_1$-$C_5$ alkyl,

  (ii)

  (iii)

  (iv)

  (v)

  (vi)

—CN,  (vii)
—Cl,  (viii)
$C_1$-$C_7$ ketone, and  (ix)

  (x)

(b) Cyclic siloxanes

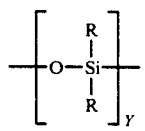

wherein (1) $Y = 1$ to 4, (2) total carbons $\leq 14$, (3) R can be independently $C_1$-$C_{10}$ alkyl or trialkyl siloxy, and (4) at least one R per molecule must be selected from $C_1$-$C_7$ hydroxyalkyl or —$R'_1$ $R_2$ wherein $R'_1 = C_1$-$C_4$ alkylene and $R_2$ is selected from

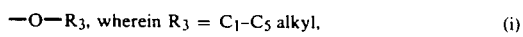  (i)

—O—$R_3$, wherein $R_3$ = $C_1$-$C_5$ alkyl,

  (ii)

  (iii)

  (iv)

-continued

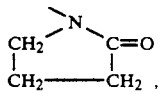 (v)

$$-\overset{O}{\overset{\|}{C}}-OH,$$ (vi)

—CN, (vii)
—Cl, (viii)
$C_1$-$C_7$ ketone, and (ix)

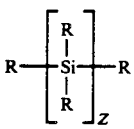 (x)

(c) Silanes

wherein (1) Z=1 to 4, (2) total carbons≦14, (3) R can be independently $C_1$-$C_{10}$ alkyl or trialkyl ($C_1$-$C_3$) siloxy, and (4) at least one R per molecule must be selected from aryl, alkylaryl, arylalkyl, $C_1$-$C_7$ hydroxyalkyl, $C_2$-$C_{10}$ alkyl, or —$R_1 R_2$ where $R_1$=$C_1$-$C_9$ alkylene (preferably $C_1$-$C_4$ alkylene) and $R_2$ is selected from $$-\overset{O}{\overset{\|}{C}}-NH_2,$$ (i)

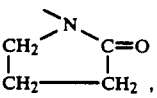 (ii)

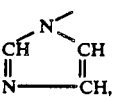 (iii)

—CN, (iv)
—$C_1$-$C_7$ ketone, (v)
—$OR_3$, (vi)

$$-\overset{O}{\overset{\|}{C}}-OH,$$ (vii)

—Cl, (viii)

$$-O-\overset{O}{\overset{\|}{C}}-R_3, \text{ and}$$ (ix)

$$-\overset{O}{\overset{\|}{C}}-O-R_3, \text{ where } R_3 = C_1\text{-}C_5 \text{ alkyl.}$$ (x)

The boiling point of all of these silicon compounds at 760 mm is ≦260° C. The aryl groups used in the silicon compounds may be substituted, for example, with —Cl or —OH moieties.

DETAILED DESCRIPTION OF THE INVENTION

The present invention, as summarized above, relates to cosmetic and household products containing silicon compounds having improved solvency and compatibility properties.

Examples of these material include, among many others, the following:

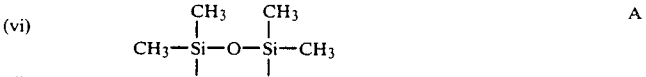 A

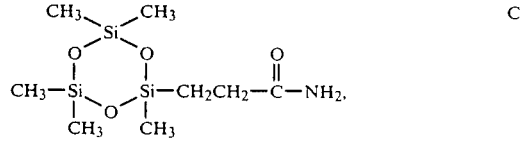 B

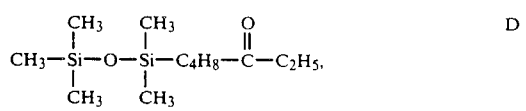 C

 D

 A$^1$

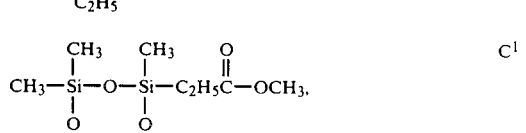 B$^1$

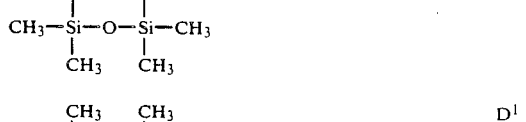 C$^1$

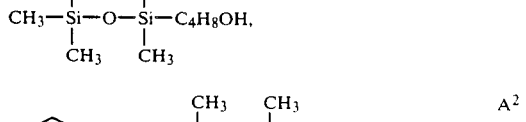 D$^1$

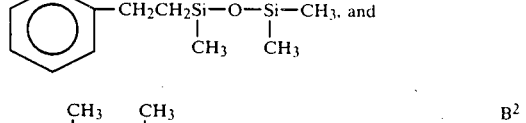 A$^2$

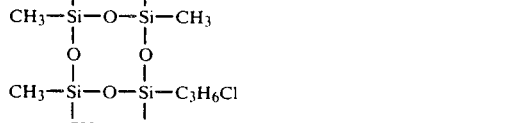 B$^2$

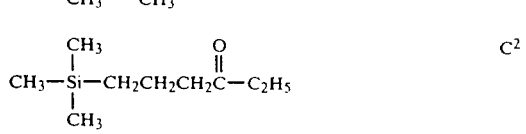 C$^2$

-continued

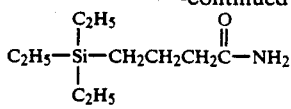
D²

Cosmetic and Household Products

The volatile silicon compounds described above find use in a number of different products. These include hair care products such as hairsprays, shampoos, mousses, styling gels and lotions, cream rinses/conditioners, hair tonics, hair dyes and colorants, home permanents and bleaches. Also included are skin care products such as cleansers, conditioners, lipsticks, eye makeup, fingernail polish, suntan products, antiperspirant/deodorant products and depilatories. Also included are household products such as waxes, polishes, heavy and light duty liquid cleaners, fabric softeners and window cleaners.

Given below are several detailed descriptions of suitable products of the type mentioned above.

Hair Care Products

The hair care products of the present invention contain the volatile silicon compounds described above along with a carrier benefiting from the silicon compound. The term "carrier", as used herein, means one or more compatible vehicles which are suitable for administration to the hair of a human or lower animal. The term "compatible", as used herein, means that the components of the carrier are capable of being commingled with the silicon compounds of the present invention, and with each other, in a manner such that there is no interaction which would substantially reduce the ability of the hair care products to provide its benefit under ordinary use situation.

Carriers suitable for use with the volatile silicon agents such as shampoos and cream rinse conditioners to hair are well known in the art, and their selection can be made without difficulty by a person skilled in the art. For example, carriers which are suitable are described in more detail in U.S. Pat. No. 3,577,517, Kubot et al., issued May 4, 1971; U.S. Pat. No. 3,907,984, Calvert et al., issued Sept. 23, 1975; U.S. Pat. No. 4,012,501, Farber, issued Mar. 15, 1977; U.S. Pat. No. 4,223,009, Chakrabarti, issued Sept. 16, 1980; and U.S. Pat. No. 4,283,384, Jacquet et al., issued Aug. 11, 1981; the disclosures of all these patents being incorporated herein by reference in their entirety.

Shampoo compositions useful with the silicon compounds of this invention utilize conventional. components. The shampoos comprise from about 0.1% to about 20% of the volatile silicon compound; from about 5% to about 60% of a synthetic surfactant; and the balance water. Suitable surfactants include ammonium lauryl sulfate, ammonium laureth sulfate, triethylamine lauryl sulfate, thiethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, lauryl sarcosine, cocoyl sarcosine, ammonium cocoyl sulfate, ammonium lauryl sulfate, sodium cocoyl sulfate, sodium lauryl sulfate, potassium cocoyl sulfate, potassium lauryl sulfate, triethanolamine cocoyl sulfate, triethanolamine lauryl sulfate, monoethanolamine cocoyl sulfate, monoethanolamine lauryl sulfate, sodium tridecyl benzene sulfonate and sodium dodecyl benzene sulfonate.

Shampoos can also contain a variety of nonessential optional components. Such conventional optional ingredients are well known to those skilled in the art, e.g., preservatives, such as benzyl alcohol, ethyl paraben, propyl paraben and imidazolidinyl urea; hair styling/setting polymers such as acrylate polymers and copolymers; cationic surfactants, such as cetyl trimethyl ammonium chloride, lauryl trimethyl ammonium chloride, tricetyl methyl ammonium chloride, stearyldimethyl benzyl ammonium chloride, and di(partially hydrogenated tallow) dimethylammonium chloride; thickeners and viscosity modifiers such as a diethanolamide of a long-chain fatty acid (e.g., PEG 3 lauramide), block polymers of ethylene oxide and propylene oxide, sodium chloride, sodium sulfate, polyvinyl alcohol, ethyl alcohol and water-soluble polymers such as xanthan gum, hydroxyethyl cellulose, guar gum and starch; pH adjusting agents, such as citric acid, succinic acid, phosphoric acid, sodium hydroxide, sodium carbonate; perfumes; dyes; and sequestering agents, such as disodium ethylenediamine tetraacetate. Such agents generally are used individually at a level of from about 0.01% to about 10%, preferably from about 0.5% to about 5.0% by weight of the composition.

Another carrier useful with the present silicon compounds are creme rinses/conditioners. Such a carrier preferably comprises two essential components: a lipid vehicle material and generally a o cationic surfactant vehicle material. Such carriers are generally described in the following documents, all incorporated by reference herein: Barry, "The Self Bodying Action of the Mixed Emulsifier copolymers; cationic surfactants, such as cetyl trimethyl ammonium Sodium Dodecyl Sulfate/Cetyl Alcohol", 28. *J. of Colloid and Interface Science* 82–91 (1968); Barry et al., "The Self-Bodying Action of Alkyltrimethylammonium Bromides/Cetostearyl Alcohol Mixed Emulsifiers; Influence of Quaternary Chain Length", 35 *J. of Colloid and Interface Science* 689–708 (1971); and Barry et al., "Rheology of Systems Containing Cetomacrogol 1000—Cetostearyl Alcohol, I. Self Bodying Action", 38 *J. of Colloid and interface Science* 616–625 (1972).

Lipid materials include naturally or synthetically-derived acids, acid derivatives, alcohols, esters, ethers, ketones, and amides with carbon chains of from 12 to 22, preferably from 16 to 18, carbon atoms in length. Fatty alcohols and fatty esters are preferred; fatty alcohols are particularly preferred.

Lipid materials among those useful herein are disclosed in Bailey's Indistrial Oil and Fat Products, (3d edition, D. Swern, ed. 1979) (incorporated by reference herein). Fatty alcohols included among those useful herein are disclosed in the following documents, all incorporated by reference herein: U.S. Pat. No. 3,155,591, Hilfer, issued Nov. 3, 1964; U.S. Pat. No. 4,165,369, Watanabe et al., issued Aug. 21, 1979; U.S. Pat. No. 4,269,824, Villamarin et al., issued May 26, 1981; British Specification 1,532,585, published Nov. 15, 1978; and Fukushima et al., "The Effect of Cetostearyl Alcohol in Cosmetic Emulsions", 98 *Cosmetics & Toiletries* 89–102 (1983). Fatty esters included among those useful herein are disclosed in U.S. Pat. No. 3,341,465, Kaufman et al., issued Sept. 12, 1967 (incorporated by reference herein).

Preferred esters for use herein include cetyl palmitate and glycerylmonostearate. Cetyl alcohol and stearyl alcohol are preferred alcohols. A particularly preferred lipid vehicle material is comprised of a mixture of cetyl alcohol and stearyl alcohol containing from about 55% to about 65% (by weight of mixture) of cetyl alcohol.

Creme rinse and conditioner compositions of the present invention generally comprise from about 0.5% to about 12% of the silicon compound, from about 0.5% to about 3% of the lipid vehicle material, and from about 0.2% to about 4% of the cationic surfactant vehicle material.

Deodorant/Antiperspirants

Deodorant/antiperspirant compositions utilizing the volatile silicon compounds include a variety of components.

Antiperspirant Actives

Antiperspirant compositions comprise at least one antiperspirant active. Antiperspirant actives useful in the present invention are well known in the art, and are disclosed generally in Miller and Hoag, "Personal Care Products", *Handbook of Nonprescription Drugs*, 8th Edition, Chapter 19, pages 397–417 (American Pharmaceutical Association; 1986), the disclosures of which are incorporated herein by reference in their entirety. Antiperspirant actives useful herein are also more specifically disclosed in European Patent Application Publication No. 28,853, published May 20, 1981, by Beckmeyer et al.; and European Patent Application Publication No. 117,070, published Aug. 29, 1984, by May, the disclosures of both these patent specifications being incorporated herein by reference in their entirety. Antiperspirant actives include, for example, aluminum chlorohydrates, aluminum chloride, sodium aluminum chlorohydroxy lactate, buffered aluminum sulfate, and aluminum zirconium chlorohydrates.

Preferred are astringent metallic salts including the inorganic and organic salts of aluminum, zirconium and zinc, and mixtures thereof. Particularly preferred are the aluminum and zirconium salts, such as aluminum halides, aluminum hydroxyhalides, zirconyl oxyhalides, zirconyl hydroxyhalides, and mixtures thereof. Such metal salts, and complexes thereof, are described in European Patent Specification Publication No. 117,070, to May, published Aug. 29, 1984, and U.S. Pat. No. 4,137,306, to Rubino et al., issued Jan. 30, 1979, the disclosures of both these patent specifications being incorporated herein by reference in their entirety.

Preferred aluminum salts include those of the formula:

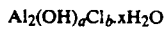

wherein a is from about 2 to about 5; $a+b=6$; x is from about 1 to about 6; and wherein a, b, and x may have non-integer values. Particularly preferred are aluminum chlorhydroxides referred to as "5/6 basic chlorhydroxide", wherein $a=5$; and "⅔ basic chlorhydroxide", wherein $a=4$. Processes for preparing aluminum salts are disclosed in the following documents, all incorporated by reference herein in their entirety: U.S. Pat. No. 3,887,692, Gilman, issued June 3, 1975; U.S. Pat. No. 3,904,741, Jones et al., issued Sept. 9, 1975; U.S. Pat. No. 4,359,456, Gosling et al., issued Nov. 16, 1982; and British Patent Specification 2,048,229, Fitzgerald et al., published Dec. 10, 1980. Mixtures of aluminum salts are described in British Patent Specification 1,347,950, Shin et al., published Feb. 27, 1974, the disclosures of which are incorporated herein by reference in their entirety.

Zirconium salts are also preferred for use in antiperspirant compositions of the present invention. Such salts are of the general formula:

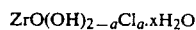

wherein a is from about 1 to about 2, preferably from about 1.5 to about 1.87; x is from about 1 to about 7; and wherein a and x may have non-integer values. These zirconium salts are disclosed in Belgium Patent Specification 825,146, Schmitz, issued Aug. 4, 1975, the disclosures. of which are incorporated herein by reference in their entirety. Particularly preferred zirconium salts are those complexes also containing aluminum and glycine, commonly known as "ZAG complexes". Such ZAG complexes contain aluminum chlorhydroxide and zirconyl hydroxychloride of the formulae detailed above. These compounds in ZAG complexes are disclosed in the following patent documents, all incorporated by reference herein in their entirety: U.S. Pat. No. 2,814,585, Daley, issued Nov. 26, 1957; U.S. Pat. No. 3,679,068, Luedders et al, issued Feb. 12, 1974; U.S. Pat. No. 4,017,599, Rubino, issued Apr. 12, 1977; U.S. Pat. No. 4,120,948, Shelton, issued Oct. 17, 1978; and British Patent Specification 2,144,992, Callaghan et al., published Mar. 20, 1985.

The antiperspirant actives in total typically comprise from about 1% to about 50% by weight of the composition of the present invention, more preferably from about 5% to about 40%, and most preferably from about 5% to about 30%.

Deodorant/Antiperspirant Carrier

The selection of carriers for use with the volatile silicon compounds of the present invention is readily made by one skilled in the art based on the form of the composition being prepared, for example, aerosol spray, roll-on lotion, or stick. Antiperspirant carriers are described in detail in European Patent Application No. 28,853, Beckmeyer et al., published May 20, 1981, and European Patent Application Publication No. 117,070, May, published Aug. 29, 1984, the disclosures of both these patent specifications being incorporated herein by reference in their entirety. Carrier materials suitable for use for various composition forms are also described in detail as follows:

(i) Stick Antiperspirant Carriers

Antiperspirant compositions in stick form contain the volatile silicon compound, which may function as a liquid emollient and preferably contain one or more non-volatile emollients. Such materials include fatty acid and fatty alcohol esters, waterinsoluble ethers and alcohols, polyorganosiloxanes, and mixtures thereof. Emollients among those useful herein are described in 1 *Cosmetics, Science and Technology* 27-104 (M. Balsam and E. Sagarin ed. 1972), and U.S. Pat. No. 4,202,879, Shelton, issued May 13, 1980 (both incorporated by reference herein).

The present compositions in stick form preferably contain a non-volatile silicone oil as an emollient material. Such silicone oils include polyalkysiloxanes, polyalkyarylsiloxanes, and polyethersiloxane copolymers. the essentially non-volatile polyalkyl siloxanes useful herein include, for example, polydimethyl siloxanes with viscosities of from about 5 to about 100,000 centistokes at 25° C. Among the preferred non-volatile emollients useful in the present compositions are the polydimethyl siloxanes having viscosities from about 10 to about 400 centistokes at 25° C. Such polyalkyl siloxanes include the Vicasil series (sold by General Electric Company) and the Dow Corning 200 series (sold by Dow Corning Corporation). Polyalkylaryl siloxanes include polymethylphenyl siloxanes having viscosities of from about 15 to about 65 centistokes at 25° C. These are available, for example as SF 1075 methylphenyl fluid (sold by General Electric Company) and 556 Cosmetic Grade Fluid (sold by Dow Corning Corporation). Useful polyether siloxane copolymers include, for example, a polyoxyalkylene ether copolymer having a viscosity of about 1200 to 1500 centistokes at 25° C. Such a fluid is available as SF-1066 organosilicone surfactant (sold by General Electric Company). Polysiloxane ethylene glycol ether copolymers are preferred copolymers for use in the present compositions.

Antiperspirant compositions in stick form further preferably contain one or more materials having wax-like characteristics and o have a melting point of from about 65° C. to about 102° C. Such waxes include beeswax, spermaceti, carnauba, baysberry, candelilla, montan, oxokerite, ceresin, paraffin, hydrogenated castor oil (castor wax), synthetic waxes such as Fisher-Tropsch waxes, microcrystalline wax, and mixtures thereof. Castor wax is a preferred high-melting point wax useful herein. Such high-melting point waxes among those useful herein are disclosed in U.S. Pat. No. 4,049,792, Elsnau, issued Sept. 20, 1977 (incorporated by reference herein).

(ii) Aerosol Spray Deodorant/Antiperspirant Carriers

Compositions in aerosol spray form preferably contain one or more volatile materials, herein "aerosol propellants", which in a gaseous state, carry the other components of the spray composition in particulate or droplet form. The aerosol propellants useful in the present invention typically have a boiling point within the range of from about −45° C. to about 5° C. The aerosol propellants are liquified when packaged in conventional aerosol containers under pressure. The rapid boiling of the aerosol propellant upon leaving the aerosol container aids in the atomization of the other components of the present invention.

Aerosol propellants useful in the compositions of the present invention in spray form include those well known in the art. Such aerosol propellants include the chemically-inert hydrocarbons such as propane, n-butane, isobutane and cyclopropane, and mixtures thereof, as well as halogenated hydrocarbons such as dichlorodifluoromethane (propellant 12), 1,1-dichloro-1,1,2,2-tetrafluoroethane (propellant 114), 1-chloro-1,1-difluoro-2,2-trifluoroethane (propellant 115), 1-chloro-1,1-difluoroethylene (propellant 142B), 1,1-difluoroethane (propellant 152A), and monochlorodifluoromethane, and mixtures thereof. Isobutane, used singly or admixed with other hydrocarbons, is preferred for use in the present aerosol spray antiperspirants.

Another preferred material for use in the aerosol compositions in aerosol spray form is a silicone gum. As referred to herein, "silicone gum" materials useful in the present compositions are those non-functionalized siloxanes having a viscosity of from about 500,000 to about 100,000,000 centistokes at 25° C. These materials are incorporated in the present compositions at a level of from about 0.05% to about 5.0%, preferably from about 0.10% to about 2.0%. Preferred silicone gums include linear and branched polydimethyl siloxanes, of the following general formula:

$(CH_3)_3SiO\text{---}Si\,(CH_3)_2\,O_n\text{---}Si(CH_3)_3$ wherein n is from about 2,000 to about 15,000, preferably from about 2,000 to about 7,000. The silicone gums useful herein may also be substituted with non-electronegative substituents. Silicone gums among those useful herein are available from a variety of commercial sources, including X2-1346 and Dow Corning 200 Fluid (manufactured by Dow Corning Corporation), PS240 (manufactured by Petrarch Systems, Inc.), and SE76, SE30 and SE32 Silicone Gums (manufactured by General Electric Company).

The aerosol compositions may also contain a bulking or suspending agent, at levels of from about 0.1% to about 7%, preferably from about 0.4% to about 3.5%. Such bulking/suspending agents include talc, colloidal silicas, clays and mixtures thereof. Clays and colloidal silicas are particularly preferred. Clay bulking/suspending agents include montmorillonite clays and hydrophobically treated montmorillonites, e.g., bentonites, hectorites and colloidal magnesium aluminum silicates. These materials are available from a variety of sources, including Laponite hectorite (sold by Laponite Industries, Ltd.) and Veegum magnesium aluminum silicate (sold by R. T. Vanderbilt Co.). A preferred clay bulking/suspending agent is hydrophobically-treated montmorillonite, such as the Bentone bentonites (sold by NL Industries, Inc.). Colloidal silicas are also readily available, such as Cab-O-Sil pyrogenic colloidal silica (sold by Cabot Corporation).

(iii) Roll-on Lotion Deodorant/Antiperspirant Carriers

Antiperspirant/deodorant compositions of the present invention in roll-on lotion form typically comprise carrier materials similar to those utilized in aerosol spray forms except that no aerosol propellant is required. Antiperspirant/deodorant compositions in roll-on lotion form, and carrier materials useful therein, are described in detail in European Patent Application Publication No. 28,853, Beckmeyer et al., published May 20, 1981, the disclosures of which are incorporated herein by reference in their entirety.

Additional active components include bacteriostats and fungistats. The particular non-active components that may be useful will depend upon the form of application that is desired. Such components include, for example, emollients, colorants, perfumes, and emulsifiers. Optional components useful herein are described in the following documents, all incorporated by reference herein: U.S. Pat. No. 4,049,792, Elsnau, issued Sept. 20, 1977; Canadian Patent 1,164,347, Beckmeyer et al., issued Mar. 27, 1984; European Patent Specification 117,070, May, published Aug. 29, 1984; and Geria, "Formulation of Stick Antiperspirants and Deodorants," 99 Cosmetics & Toiletries 55–60 (1984).

Generally, the deodorant/antiperspirant carriers in total comprise from about 40% to about 99% by weight of the compositions of the present invention, preferably from about 55% to about 95%, and most preferably from about 67% to about 94%.

Other cosmetic and household product compositions are disclosed in U.S. Pat. No. 4,687,592, Collins et al., issued Aug. 18, 1987; U.S. Pat. No. 4,663,157, Brock, issued May 5, 1987; U.S. Pat. No. 4,631,064, Juneja;

issued Dec. 23, 1986; and U.S. Pat. No. 4,130,121, Wetzel, issued Dec. 19, 1978. All of these references are incorporated herein by reference.

METHOD OF MANUFACTURE OF VOLATILE SILICONS

The compositions of the present invention can be prepared by methods which are well known in the art.

The following nonlimiting examples of the present invention are given solely for illustration and are not to be construed as limitations of this invention. Many variations are possible without departing from the spirit and scope thereof. The volatile silicon compounds in the various examples are identified in previous discussion.

EXAMPLE I

The following is a highlighting rinse representative of the present invention:

| Component | Weight % |
| --- | --- |
| D & C Red #17 | 0.10 |
| Volatile Silicon Compound A | 5.00 |
| Cetyl Alcohol | 2.00 |
| Ditallow Dimethyl Ammonium Chloride | 1.00 |
| Ceteareth-20 | 1.00 |
| Kathon CG | 0.04 |
| Double Reverse Osmosis Water | q.s |

EXAMPLE II

The following is a shampoo representative of the present invention.

| Component | Weight % |
| --- | --- |
| Ammonium Lauryl Sulfate | 15.00 |
| Jaguar HP-60[1] | 1.00 |
| G.E. SE 30[2] | 1.00 |
| Volatile Silicon Compound D | 1.00 |
| Kathon CG[3] | 0.04 |
| Double Reverse Osmosis Water | q.s. |

[1]Hydroxypropyl guar gum offered by Hi-tek Polymers Inc.
[2]Silicone gum offered by General Electric
[3]Offered by Rohm and Haas

EXAMPLE III

The following is a men's grooming aid representative of the present invention.

| Component | Weight % |
| --- | --- |
| Volatile Silicon Compound C | 86.00 |
| Dow Corning X2-2G13[1] | 8.00 |
| Perfume | 1.00 |
| Ethanol | 5.00 |

[1]A copolymer of methyl-phenyl and diphenyl siloxane offered by Dow Corning

EXAMPLE IV

The following is a hair styling mousse representative of the present invention.

| Component | Weight % |
| --- | --- |
| Gafquat 755 | 2.00 |
| Cocamine oxide | 0.50 |
| Kathon CG | 0.04 |
| Volatile Silicon Compound C | 2.00 |
| Isobutane | 6.00 |
| Distilled Water | q.s. |

EXAMPLE V

The following is a hair conditioning rinse representative of the present invention.

| Component | Weight % |
| --- | --- |
| Stearalkonium Chloride | 2.00 |
| Stearyl Alcohol | 0.90 |
| Cetyl Alcohol | 1.10 |
| Volatile Silicon Compound B | 4.00 |
| G.E. SE 30 Silicone Gum | 1.00 |
| Kathon CG[1] | 0.04 |
| Distilled Water | q.s. |

[1]Offered by Rohm and Haas

EXAMPLE VI

The following is a hairspray composition representative of the present invention.

| Component | Weight % |
| --- | --- |
| Amphomer | 3.00 |
| Aminomethyl propanol | 0.50 |
| Volatile Silicon Compound C | 1.00 |
| Ethanol | 70.5 |
| Isobutane Propellant | 25.00 |

EXAMPLE VII

The following is a cold-wave hair perm representative of the present invention.

| Component | Weight % |
| --- | --- |
| Thioglycolic Acid | 7.00 |
| Monoethanolamine | 9.00 |
| Volatile Silicon Compound C | 3.00 |
| Polyethylene Glycol 400 Monostearate | 0.50 |
| Distilled Water | q.s. |

EXAMPLE VIII

The following is a cologne representative of the present invention.

| Component | Weight % |
| --- | --- |
| Volatile Silicon Compound A | 45.00 |
| Propylene Glycol | 2.00 |
| Perfume | 2.00 |
| Polydimethylsiloxane 350 cs. | 1.00 |
| Isobutane | 50.00 |

EXAMPLE IX

The following is an antiperspirant stick representative of the present invention.

| Component | Weight % |
| --- | --- |
| Crodomol PMP[1] | 15.00 |
| Syncrowax BB4[1] | 1.50 |
| Incroquat Behenyl TMS[2] | 12.00 |
| Incromide BEM[2] | 12.00 |

| Component | Weight % |
|---|---|
| Volatile Silicon Compound D | 37.00 |
| Rezel 36q Superultrafine[3] | 20.00 |
| Talc | 1.00 |
| Cab-O-Sil M-5[4] | 1.50 |

[1]Offered by Croda, Inc.
[2]Offered by Croda Surfactants, Inc.
[3]Offered by Reheis Chemical Company
[4]Offered by Cabot Corporation

EXAMPLE X

The following is a solid deodorant representative of the present invention.

| Component | Weight % |
|---|---|
| Volatile Silicon Compound B | 39.00 |
| Sodium Stearate | 9.00 |
| Propylene Glycol | 15.00 |
| Ethanol | q.s. |
| PPG-10 Cetyl Ether | 10.00 |
| Isostearyl Alcohol | 3.00 |
| Perfume | 0.50 |

EXAMPLE XI

The following is a roll-on antiperspirant representative of the present invention.

| Component | Weight % |
|---|---|
| Volatile Silicon Compound A | 64.60 |
| Isopropyl Myristate | 5.00 |
| Tixogel VP[1] | 3.00 |
| Aluminum Zirconium Trichlorohydrate | 25.00 |
| Ethanol (95%/5% water) | 2.00 |
| Perfume | 0.10 |
| Cab-O-Sil M-5[2] | 0.30 |

[1]Offered by United Catalysts Inc.
[2]Offered by Cabot

EXAMPLE XII

The following is a hand lotion representative of the present invention.

| Component | Weight % |
|---|---|
| Volatile Silicon Compound D | 3.00 |
| Mineral Oil | 1.00 |
| Polydimethylsiloxane, 350 C | 1.00 |
| Stearic Acid | 3.00 |
| Cetyl Alcohol | 2.00 |
| Triethanolamine | 1.00 |
| Glydant | 0.35 |
| Glycerine | 5.00 |
| Carbopol 941[1] | 0.20 |
| Distilled Water | q.s. |

[1]Offered by B. F. Goodrich

What is claimed is:
1. A cosmetic or household composition comprising:
(a) a suitable carrier; and
(b) a volatile silicon compound selected from the group consisting of
(I) linear siloxanes

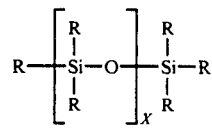

wherein (1) X=1 to 4, (2) total carbons $\leq 14$, (3) R can be independently $C_1$-$C_{10}$ alkyl or trialkyl ($C_1$-$C_3$) Siloxy, and (4) at least one R per molecule must be selected from aryl, alkylaryl, aryl alkyl, $C_1$-$C_7$ hydroxyalkyl, or —$R_1$ $R_2$ wherein $R_1$=$C_1$-$C_9$ alkylene and $R_2$ is selected from

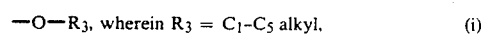  (i)

  (ii)

  (iii)

  (iv)

  (v)

  (vi)

—CN,  (vii)
—Cl,  (viii)
$C_1$-$C_7$ [ketone] keto groups, and  (ix)

  (x)

(II) cyclic siloxanes

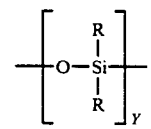

wherein (1) Y=1 to 4, (2) total carbons $\leq 14$, (3) R can be independently $C_1$-$C_{10}$ alkyl or trialkyl ($C_1$-$C_3$) siloxy, and (4) at least one R per molecule must be selected from $C_1$-$C_7$ hydroxyalkyl or —$R'_1$ $R_2$ wherein $R'_1$=$C_1$-$C_4$ alkylene and $R_2$ is selected from —O—$R_3$ wherein $R_3$ = $C_1$-$C_5$ alkyl,  (i)

  (ii)

  (iii)

-continued

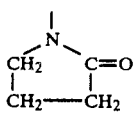

—CN,
—Cl,
C$_1$-C$_7$ [ketone] keto groups, and

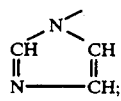

(III) silanes

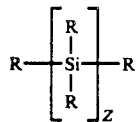

wherein (1) Z=1 to 4, (2) total carbons ≦14, (3) R can be independently C$_1$-C$_{10}$ alkyl or trialkyl (C$_1$-C$_3$) siloxy, and (4) at least one R per molecule must be selected from aryl, alkylaryl, arylalkyl, C$_1$-C$_7$ hydroxyalkyl, C$_2$-C$_{10}$ alkyl, or —R$_1$ R$_2$ where R$_1$=C$_1$-C$_9$ alkylene and R$_2$ is selected from

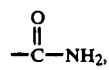 (i)

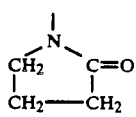 (ii)

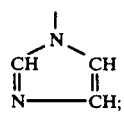 (iii)

—CN, (iv)
C$_1$-C$_7$ [ketone] keto groups, (v)

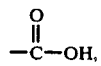 (vi)

—Cl, (vii)

 (viii)

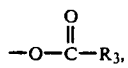 (ix)

—O—R$_3$ wherein R$_3$ = C$_1$-C$_5$ alkyl; (x)

wherein the boiling point of all these silicon compounds at 760 mm is ≦260° C.

2. A composition according to claim 1 in the form of a hair care product selected from the group consisting of hairsprays, shampoos, mousses, styling gels, styling lotions, cream rinses, conditioners, hair tonics hair dyes, hair colorants, home permanents, and hair bleaches.

3. A composition according to claim 1 in the form of a stick, roll-on or aerosol antiperspirant.

4. A composition according to claim 1 in the form of a household cleaning product selected from the group consisting of waxes, polishes, heavy duty liquid cleaners, light duty liquid cleaners, fabric softeners, and window cleaners.

5. A composition according to claim 2 wherein the volatile silicon compound is selected from

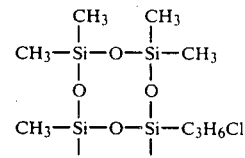

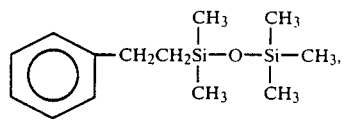

and mixtures thereof.

6. A composition according to claim 5 in the form of a shampoo which comprises from about 0.1% to about 20% of said volatile silicon compound, from about 5% to about 60% of a synthetic surfactant, and the balance water.

7. A composition according to claim 5 in the form of a hair conditioner which comprises from about 0.5% to about 12% of said volatile silicon compound, from about 0.5% to about 3% of a lipid vehicle material, and from about 0.2% to about 4% of a cationic surfactant vehicle material.

8. A composition according to claim 7 which in addition contains from about 0.01 to about 10% of a hair styling polymer.

9. A composition according to claim 2 wherein the volatile silicon compound is methoxy ethyl heptamethyl cyclotetrasiloxane.

10. A composition according to claim 3 in the form of a stick antiperspirant which comprises from about 1% to about 50% of said volatile silicon compound, from about 1% to about 50% of an antiperspirant active, and the remainder being a carrier selected from the group consisting of non-volatile emollients, waxes, perfumes, colorants, and mixtures thereof.

11. A composition according to claim 3 in the form of a roll-on antiperspirant which comprises from about 1% to about 50% of said volatile silicon compound, from about 1% to about 50% of an antiperspirant active, and the remainder being a carrier selected from the group consisting of emollients, colorants, perfumes, emulsifiers, and mixtures thereof.

* * * * *